United States Patent
Ye et al.

(10) Patent No.: US 10,266,882 B2
(45) Date of Patent: Apr. 23, 2019

(54) HUMAN RARE BLOOD GROUP MULTIPLEX PCR DETECTION METHOD AND KIT

(75) Inventors: Luyi Ye, Shanghai (CN); Ziyan Zhu, Shanghai (CN); Zhonghui Guo, Shanghai (CN); Yunlei He, Shanghai (CN); Huanhuan Gao, Shanghai (CN); Pan Wang, Shanghai (CN); Li Xie, Shanghai (CN); Aoxue Zhu, Shanghai (CN); Wei Zhang, Shanghai (CN); Wenjie Gao, Shanghai (CN); Qixiu Yang, Shanghai (CN)

(73) Assignee: SHANGHAI BLOOD CENTRE, Changning District, Shanghai (CN)

( * ) Notice: Subject to any disclaimer, the term of this patent is extended or adjusted under 35 U.S.C. 154(b) by 239 days.

(21) Appl. No.: 14/343,046

(22) PCT Filed: Jan. 18, 2012

(86) PCT No.: PCT/CN2012/070522
§ 371 (c)(1),
(2), (4) Date: Mar. 5, 2014

(87) PCT Pub. No.: WO2013/107005
PCT Pub. Date: Jul. 25, 2013

(65) Prior Publication Data
US 2014/0221246 A1 Aug. 7, 2014

(51) Int. Cl.
*C12Q 1/68* (2018.01)
*C12Q 1/686* (2018.01)
*C12Q 1/6881* (2018.01)

(52) U.S. Cl.
CPC ........... *C12Q 1/686* (2013.01); *C12Q 1/6881* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2004/0023207 A1* 2/2004 Polansky ............... A61K 31/00
435/5

OTHER PUBLICATIONS

Denomme GA, Van Oene M. High-throughput multiplex single-nucleotide polymorphism analysis for red cell and platelet antigen genotypes. Transfusion. May 2005; 45(5):660-6.*

Deng, Shi-zhen, Kang-feng Yan, and Jing-wen Xie. Application of Multiple PCR for Screening S, Fya, OKa Negative Rare Blood Type. Chinese Journal of General Practice (May 2012): 10(5): pp. 785-786.*

He YL, Gao HH, Ye LY, Guo ZH, Wang P, Zhu ZY. Multiplex polymerase chain reaction with DNA pooling: a cost-effective strategy of genotyping rare blood types. Transfus Med. Feb. 2013; 23(1):42-7. Epub Oct. 29, 2012*

Wagner FF, Bittner R, Petershofen EK, Doescher A, Müller TH. Cost-efficient sequence-specific priming-polymerase chain reaction screening for blood donors with rare phenotypes. Transfusion. Jun. 2008; 48(6):1169-73. Epub Apr. 15, 2008.*

Yan, Kang-feng, Shi-zhen Deng, and Jing-wen Xie. Multiple PCR for Screening Coa, Lub, Yta, Kpb Negative Rare Blood Type. Chinese Journal of General Practice (Sep. 2011): 9(9):1454.*

Ye L, Yue D, Wo D, Ding X, Guo S, Li Q, Guo Z, Zhu Z. Molecular bases of unexpressed RHD alleles in Chinese D-persons. Transfusion. Aug. 2009; 49(8):1655-60.*

Ye L, Wang P, Gao H, Zhang J, Wang C, Li Q, Han S, Guo Z, Yang Y, Zhu Z. Partial D phenotypes and genotypes in the Chinese population. Transfusion. Feb. 2012; 52(2):241-6. Epub Jul. 25, 2011.*

Gassner C, Kleinrath T, Reiter S, Kilga-Nogler S, Schoenitzer D. Multiplex PCR-SSP screening for Kpa, Lua, Dia, Wra, Ytb, Cob, Knb, Vw and Mg. Transfus Med Hemother 2005;32 Suppl 1:1-92 Abstract 7.1. (Year: 2005).*

Londero D, Fiorino M, Miotti V, de Angelis V. Molecular RH blood group typing of serologically D−/CE+ donors: the use of a polymerase chain reaction-sequence-specific primer test kit with pooled samples. Immunohematology. 2011; 27(1):25-8. (Year: 2011).*

Wagner FF. Screening Donors for Rare Antigen Constellations. Transfus Med Hemother. 2009; 36(3):199-203. Epub May 26, 2009. (Year: 2009).*

Prager M. Molecular genetic blood group typing by the use of PCR-SSP technique. Transfusion. Jul. 2007; 47(1 Suppl):54S-9S. (Year: 2007).*

Smart EA, Storry JR. The OK blood group system: a review. Immunohematology. 2010; 26(3):124-6. (Year: 2010).*

\* cited by examiner

*Primary Examiner* — Gary Benzion
*Assistant Examiner* — Olayinka A Oyeyemi
(74) *Attorney, Agent, or Firm* — Global IP Services; Tianhua Gu

(57) ABSTRACT

Disclosed are a human rare blood type detection method, a kit, a rapid screening method and applications thereof. By using multiple pairs of PCR specific primers directing to the SNP loci of multiple rare blood types, the SNP loci of multiple rare blood types are simultaneously detected in the same PCR reaction system; and the multiplex PCR detection method and a Pool detection method are combined to rapidly screen the human rare blood types.

8 Claims, 4 Drawing Sheets
Specification includes a Sequence Listing.

SEQUENCE LISTING

<160> NUMBER OF SEQ ID NOS: 42

<210> SEQ ID NO 1
<211> LENGTH: 21
<212> TYPE: DNA
<213> ORGANISM: Artificial
<220> FEATURE:
<223> OTHER INFORMATION: PRIMER

<400> SEQUENCE: 1
tcatcaacgc gggagactta a                                      21

<210> SEQ ID NO 2
<211> LENGTH: 18
<212> TYPE: DNA
<213> ORGANISM: Artificial
<220> FEATURE:
<223> OTHER INFORMATION: PRIMER

<400> SEQUENCE: 2
cacggggcac acgacatt                                          18

<210> SEQ ID NO 3
<211> LENGTH: 22
<212> TYPE: DNA
<213> ORGANISM: Artificial

-continued

```
<220> FEATURE:
<223> OTHER INFORMATION: PRIMER

<400> SEQUENCE: 3
cttccttaaa ctttaaccgc at                                              22

<210> SEQ ID NO 4
<211> LENGTH: 20
<212> TYPE: DNA
<213> ORGANISM: Artificial
<220> FEATURE:
<223> OTHER INFORMATION: PRIMER

<400> SEQUENCE: 4
cccaacctgc aaccttcctc                                                 20

<210> SEQ ID NO 5
<211> LENGTH: 22
<212> TYPE: DNA
<213> ORGANISM: Artificial
<220> FEATURE:
<223> OTHER INFORMATION: PRIMER

<400> SEQUENCE: 5
tgtcaatctc catcacttca aa                                              22

<210> SEQ ID NO 6
<211> LENGTH: 20
<212> TYPE: DNA
<213> ORGANISM: Artificial
<220> FEATURE:
<223> OTHER INFORMATION: PRIMER

<400> SEQUENCE: 6
tcctccacca gttgtgacat                                                 20

<210> SEQ ID NO 7
<211> LENGTH: 21
<212> TYPE: DNA
<213> ORGANISM: Artificial
<220> FEATURE:
<223> OTHER INFORMATION: PRIMER

<400> SEQUENCE: 7
gtgggtggtg aagtccaatc t                                               21

<210> SEQ ID NO 8
<211> LENGTH: 21
<212> TYPE: DNA
<213> ORGANISM: Artificial
<220> FEATURE:
<223> OTHER INFORMATION: PRIMER

<400> SEQUENCE: 8
agagggtctg gctgtcttga a                                               21

<210> SEQ ID NO 9
<211> LENGTH: 22
<212> TYPE: DNA
<213> ORGANISM: Artificial
<220> FEATURE:
<223> OTHER INFORMATION: PRIMER

<400> SEQUENCE: 9
tactcctgcg tcttcctcaa ca                                              22
```

```
<210> SEQ ID NO 10
<211> LENGTH: 21
<212> TYPE: DNA
<213> ORGANISM: Artificial
<220> FEATURE:
<223> OTHER INFORMATION: PRIMER

<400> SEQUENCE: 10
ctccccctcg ttgatgtgtt c                                              21

<210> SEQ ID NO 11
<211> LENGTH: 21
<212> TYPE: DNA
<213> ORGANISM: Artificial
<220> FEATURE:
<223> OTHER INFORMATION: PRIMER

<400> SEQUENCE: 11
ggtggggaac aaccagagcg t                                              21

<210> SEQ ID NO 12
<211> LENGTH: 24
<212> TYPE: DNA
<213> ORGANISM: Artificial
<220> FEATURE:
<223> OTHER INFORMATION: PRIMER

<400> SEQUENCE: 12
cctccagcaa cctcttgtcc tctc                                           24

<210> SEQ ID NO 13
<211> LENGTH: 21
<212> TYPE: DNA
<213> ORGANISM: Artificial
<220> FEATURE:
<223> OTHER INFORMATION: PRIMER

<400> SEQUENCE: 13
cttcccagat ggagactatc a                                              21

<210> SEQ ID NO 14
<211> LENGTH: 21
<212> TYPE: DNA
<213> ORGANISM: Artificial
<220> FEATURE:
<223> OTHER INFORMATION: PRIMER

<400> SEQUENCE: 14
aacaagacaa agatggcaag a                                              21

<210> SEQ ID NO 15
<211> LENGTH: 21
<212> TYPE: DNA
<213> ORGANISM: Artificial
<220> FEATURE:
<223> OTHER INFORMATION: PRIMER

<400> SEQUENCE: 15
tgatagccgc atgacccttc t                                              21

<210> SEQ ID NO 16
<211> LENGTH: 20
<212> TYPE: DNA
<213> ORGANISM: Artificial
<220> FEATURE:
<223> OTHER INFORMATION: PRIMER
```

<400> SEQUENCE: 16
acgatggaca agttgtccga                                        20

<210> SEQ ID NO 17
<211> LENGTH: 21
<212> TYPE: DNA
<213> ORGANISM: Artificial
<220> FEATURE:
<223> OTHER INFORMATION: PRIMER

<400> SEQUENCE: 17
ttccctcctc agatcattgc t                                      21

<210> SEQ ID NO 18
<211> LENGTH: 21
<212> TYPE: DNA
<213> ORGANISM: Artificial
<220> FEATURE:
<223> OTHER INFORMATION: PRIMER

<400> SEQUENCE: 18
tcaccttcac cgttccagtt t                                      21

<210> SEQ ID NO 19
<211> LENGTH: 18
<212> TYPE: DNA
<213> ORGANISM: Artificial
<220> FEATURE:
<223> OTHER INFORMATION: PRIMER

<400> SEQUENCE: 19
cggcatcgtc accaactg                                          18

<210> SEQ ID NO 20
<211> LENGTH: 19
<212> TYPE: DNA
<213> ORGANISM: Artificial
<220> FEATURE:
<223> OTHER INFORMATION: PRIMER

<400> SEQUENCE: 20
tgcaaagaac acggctaag                                         19

<210> SEQ ID NO 21
<211> LENGTH: 21
<212> TYPE: DNA
<213> ORGANISM: Artificial
<220> FEATURE:
<223> OTHER INFORMATION: PRIMER

<400> SEQUENCE: 21
ctctgcctga catgagggtt a                                      21

<210> SEQ ID NO 22
<211> LENGTH: 21
<212> TYPE: DNA
<213> ORGANISM: Artificial
<220> FEATURE:
<223> OTHER INFORMATION: PRIMER

<400> SEQUENCE: 22
tcaccttcac cgttccagtt t                                      21

<210> SEQ ID NO 23

<211> LENGTH: 21
<212> TYPE: DNA
<213> ORGANISM: Artificial
<220> FEATURE:
<223> OTHER INFORMATION: PRIMER

<400> SEQUENCE: 23
tcctccttgg acgtgtacga t          21

<210> SEQ ID NO 24
<211> LENGTH: 21
<212> TYPE: DNA
<213> ORGANISM: Artificial
<220> FEATURE:
<223> OTHER INFORMATION: PRIMER

<400> SEQUENCE: 24
ctcctctgcc gtgtagtttc g          21

<210> SEQ ID NO 25
<211> LENGTH: 21
<212> TYPE: DNA
<213> ORGANISM: Artificial
<220> FEATURE:
<223> OTHER INFORMATION: PRIMER

<400> SEQUENCE: 25
ttatgccaga atcaggttag a          21

<210> SEQ ID NO 26
<211> LENGTH: 21
<212> TYPE: DNA
<213> ORGANISM: Artificial
<220> FEATURE:
<223> OTHER INFORMATION: PRIMER

<400> SEQUENCE: 26
gagagaagga atgtacggga g          21

<210> SEQ ID NO 27
<211> LENGTH: 21
<212> TYPE: DNA
<213> ORGANISM: Artificial
<220> FEATURE:
<223> OTHER INFORMATION: PRIMER

<400> SEQUENCE: 27
caagccaccc aagtatcacc c          21

<210> SEQ ID NO 28
<211> LENGTH: 21
<212> TYPE: DNA
<213> ORGANISM: Artificial
<220> FEATURE:
<223> OTHER INFORMATION: PRIMER

<400> SEQUENCE: 28
catcccgacc ttcctcctca t          21

<210> SEQ ID NO 29
<211> LENGTH: 20
<212> TYPE: DNA
<213> ORGANISM: Artificial
<220> FEATURE:
<223> OTHER INFORMATION: PRIMER

<400> SEQUENCE: 29
aaagcctatt agagcaacgg                                                    20

<210> SEQ ID NO 30
<211> LENGTH: 21
<212> TYPE: DNA
<213> ORGANISM: Artificial
<220> FEATURE:
<223> OTHER INFORMATION: PRIMER

<400> SEQUENCE: 30
cctagaggtg gtttatttgg a                                                  21

<210> SEQ ID NO 31
<211> LENGTH: 21
<212> TYPE: DNA
<213> ORGANISM: Artificial
<220> FEATURE:
<223> OTHER INFORMATION: PRIMER

<400> SEQUENCE: 31
agagtccctt atccctatgc c                                                  21

<210> SEQ ID NO 32
<211> LENGTH: 21
<212> TYPE: DNA
<213> ORGANISM: Artificial
<220> FEATURE:
<223> OTHER INFORMATION: PRIMER

<400> SEQUENCE: 32
acctcaccag gaaatccagt c                                                  21

<210> SEQ ID NO 33
<211> LENGTH: 20
<212> TYPE: DNA
<213> ORGANISM: Artificial
<220> FEATURE:
<223> OTHER INFORMATION: PRIMER

<400> SEQUENCE: 33
gcacaggtgg aacagtaagg                                                    20

<210> SEQ ID NO 34
<211> LENGTH: 21
<212> TYPE: DNA
<213> ORGANISM: Artificial
<220> FEATURE:
<223> OTHER INFORMATION: PRIMER

<400> SEQUENCE: 34
ggttgtcaag atggtcccta a                                                  21

<210> SEQ ID NO 35
<211> LENGTH: 25
<212> TYPE: DNA
<213> ORGANISM: Artificial
<220> FEATURE:
<223> OTHER INFORMATION: PRIMER

<400> SEQUENCE: 35
ggtaagatgg cacatggaca aaggc                                              25

<210> SEQ ID NO 36
<211> LENGTH: 22
<212> TYPE: DNA

```
<213> ORGANISM: Artificial
<220> FEATURE:
<223> OTHER INFORMATION: PRIMER

<400> SEQUENCE: 36
ctgcggcgaa cctctgcttt ag                                              22

<210> SEQ ID NO 37
<211> LENGTH: 20
<212> TYPE: DNA
<213> ORGANISM: Artificial
<220> FEATURE:
<223> OTHER INFORMATION: PRIMER

<400> SEQUENCE: 37
tcacagctgt tccagtttct                                                 20

<210> SEQ ID NO 38
<211> LENGTH: 20
<212> TYPE: DNA
<213> ORGANISM: Artificial
<220> FEATURE:
<223> OTHER INFORMATION: PRIMER

<400> SEQUENCE: 38
agtgatggag attgacaagg                                                 20

<210> SEQ ID NO 39
<211> LENGTH: 25
<212> TYPE: DNA
<213> ORGANISM: Artificial
<220> FEATURE:
<223> OTHER INFORMATION: PRIMER

<400> SEQUENCE: 39
gactgggaca gttttgcttt ttcac                                           25

<210> SEQ ID NO 40
<211> LENGTH: 25
<212> TYPE: DNA
<213> ORGANISM: Artificial
<220> FEATURE:
<223> OTHER INFORMATION: PRIMER

<400> SEQUENCE: 40
gtctccccct cgttgatgtg ttctg                                           25

<210> SEQ ID NO 41
<211> LENGTH: 21
<212> TYPE: DNA
<213> ORGANISM: Artificial
<220> FEATURE:
<223> OTHER INFORMATION: PRIMER

<400> SEQUENCE: 41
catgggcttg gggaggaaga c                                               21

<210> SEQ ID NO 42
<211> LENGTH: 21
<212> TYPE: DNA
<213> ORGANISM: Artificial
<220> FEATURE:
<223> OTHER INFORMATION: PRIMER
```

```
<400> SEQUENCE: 42
ggcacggcca acatccagct c                                                    21
```

HUMAN RARE BLOOD GROUP MULTIPLEX PCR DETECTION METHOD AND KIT

BACKGROUND OF THE PRESENT INVENTION

Field of Invention

The present invention relates to the field of molecular biology, specifically to a human rare blood group detection method, kit, rapid screening method and application.

Description of Related Arts

Rare blood group antigen is a blood group antigen whose frequency in the public is less than one-thousandth, and due to its scarcity, in blood transfusion of patients of a rare blood group, it is difficult to find the source of matched blood, resulting in delay of treatment. Thus, rare blood group detection, rapid screening and establishment of a rare blood group bank are extremely important.

The existing rare blood group detection method mainly includes:

1. Serological Methods (1) Use human polyclonal sera, take advantage of the saline agglutination test or indirect antiglobulin test to perform rare blood group detection by a tube method, a U-shaped 96-well microtiter plate method or a gel method.

(2) Use animal origin (mainly murine) monoclonal or polyclonal antibody reagents of IgM-type or IgG-type, take advantage of the saline agglutination test or indirect antiglobulin test to perform rare blood group detection by a tube method, a U-shaped 96-well microtiter plate method or a gel method.

(3) For special Jk(a−b−) phenotype, a Urea method can be used. Jk(a−b−) phenotype red blood cell (RBC) may maintain the membrane integrity for 30 minutes in a 2M urea solution, and whether to be Jk(a−b−) phenotype is judged according to whether a subject RBC is hemolysis in the 2M urea solution after 10 minutes.

2. Molecular Biology Methods: Design Based on the RBC Antigen SNPs (1) Middle and low-throughput genotyping: including PCR-RFLP, PCR-SSP, real-time quantitative PCR, and pyrosequencing techniques.

(2) High-throughput genotyping: including commercial or non-commercial Beadchip, BloodChip, GenomeLab SNP stream, Luminex xMAP, and solid-phase hybridization techniques.

3. Review: the rare blood group samples obtained through screening with the above two methods generally should be reviewed through serological methods such as saline agglutination test or indirect antiglobulin test.

The existing rare blood group detection method has the following problems:

1) Serological methods: it is difficult for the majority of RBC rare blood group antigens to obtain human antibody or commercialization detection reagent, or as reagent price is too high and screening is costly, it is difficult to achieve large-scale high-throughput screening.

2) Molecular biology methods: middle and low-throughput genotyping methods are often time-consuming, and thus it is difficult to achieve large-scale high-throughput screening. The existing high-throughput genotyping methods are expensive. And the existing genotyping methods detect a single specimen, and detection costs will undoubtedly increase.

Therefore, finding a fast, economical, efficient rare blood group detection and screening method is of great practical significance.

SUMMARY OF THE PRESENT INVENTION

The present invention discloses a human rare blood group detection method, kit, rapid screening method and application, which makes that a human rare blood group PCR detection result is that positive is detectable through special design of primers and with a multiplex PCR method, and achieves efficient screening of human rare blood group.

One objective of the present invention is to provide a human rare blood group multiplex PCR detection method, taking a DNA template extracted from blood samples as a sample to be tested, using multiple pairs of specific primers for multiplex PCR amplification, and detecting amplification results through electrophoresis; wherein the specific primers are specific primers for rare blood group antigen SNP loci on blood cell surface antigen coding genes; and an electrophoresis result of the multiplex PCR detection method is that positive is detectable.

The multiplex PCR detection method according to the present invention includes multiple pairs of specific primers, each pair of specific primers are directed to a rare blood group surface antigen, and blood cell surface antigen gene fragments containing the rare blood group antigen SNP loci are amplified.

Preferably, a sequence of the multiple pairs of specific primers is SEQ ID NO: 1-6, SEQ ID NO: 7-12 or SEQ ID NO: 13-16.

That positive is detectable in the present invention means: DNA templates of rare blood group blood samples, or DNA templates of heterozygous non-rare blood group blood samples containing rare blood group antigen SNP loci could be identified by specificity of primers designed by the present invention, and are large-scale-amplified through a PCR method, it is positive if electrophoresis shows a strip emerges at a location corresponding to a rare blood group; while DNA templates of homozygous non-rare blood group blood samples could not be identified by primers and amplified, and electrophoresis shows no rare blood group strip emerges. That is, it is positive in the presence of a strip.

Relatively, that negative is detectable means: the DNA templates of homozygous or heterozygous non-rare blood group (common blood group) samples could be identified by specific primers correspondingly designed, and are large-scale-amplified through a PCR method, it is negative if electrophoresis shows a strip emerges at a location corresponding to a non-rare blood group; while DNA templates of rare blood group blood samples could not be identified by primers and amplified (rare blood group genotype is homozygous), and it is positive if electrophoresis shows no rare blood group strip emerges. That is, it is negative in the presence of a strip.

Preferably, the human rare blood group multiplex PCR detection method specifically includes:

1) preparing a sample to be tested: collecting blood samples, and extracting DNA templates as a sample to be tested;

2) preparing a multiplex PCR reaction system: the multiplex PCR reaction system includes multiple pairs of specific primers, PCR buffer solution, dNTP, Taq enzyme and ddH$_2$O, and sequences of the multiple pairs of specific primers is SEQ ID NO: 1-6, SEQ ID NO: 7-12 or SEQ ID NO: 13-16;

3) adding the sample to be tested prepared in step 1) to the multiplex PCR reaction system prepared in step 2), to obtain a PCR reaction solution;

4) performing amplification reaction on the PCR reaction solution in step 3) according to a multiplex PCR amplification procedure;

5) performing electrophoresis on amplification products obtained from the amplification reaction in step 4) in agarose gel, and observing the results through a gel imager; and 6) judging a detection result: if electrophoresis shows emergence of a strip, a detection result of a rare blood group is positive; and if electrophoresis shows no strip, the detection result of the rare blood group is negative.

Preferably, in the multiplex PCR reaction system in step 2), the multiplex PCR reaction system with primer sequences of SEQ ID NO: 1-6 is a Yt-K-Kpc system which is used on the detection for three rare blood groups: Yt(b+), K and Kp(c+); the multiplex PCR reaction system with primer sequences of SEQ ID NO: 7-12 is a Dia-OK-Cob system which is used on the detection for three rare blood groups: Di(a+), OK(a−) and Co(b+); and the multiplex PCR reaction system with primer sequences of SEQ ID NO: 13-16 is an Fyb-S system which is used on the detection for two rare blood groups: Fy(b+) and S.

Preferably, the human rare blood group multiplex PCR detection method specifically includes:

1) preparing a sample to be tested: collecting blood samples, and extracting DNA templates as a sample to be tested;

2) preparing a multiplex PCR reaction system: the multiplex PCR reaction system includes multiple pairs of specific primers, PCR buffer solution, dNTP, Taq enzyme and ddH$_2$O, and sequences of the multiplex pairs of specific primers are SEQ ID NO: 1-6, SEQ ID NO: 7-12 or SEQ ID NO: 13-16;

3) adding the sample to be tested prepared in step 1) and a built positive control to the separate multiplex PCR reaction system prepared in step 2), to obtain PCR reaction solutions;

4) performing amplification reaction on the PCR reaction solutions in step 3) according to a multiplex PCR amplification procedure;

5) performing electrophoresis on amplification products obtained from the amplification reaction in step 4) in agarose gel, and observing the results through a gel imager; and 6) judging a detection result: if electrophoresis shows a strip emerges at a location corresponding to a strip of positive control amplification, a detection result of a rare blood group is positive; and if electrophoresis shows no strip emerges at the location corresponding to the strip of positive control amplification, the detection result of the rare blood group is negative.

More preferably, the positive control is plasmid containing a rare blood group SNP loci gene fragment, and the positive control is capable of being amplified by a pair of specific primers in the multiple pairs of specific primers with a sequence of SEQ ID NO: 1-16.

Preferably, the multiplex PCR reaction system in step 2) further includes internal control primers; and the judging a detection result in step 6) is: if electrophoresis shows a rare blood group strip and an internal control strip emerge, a detection result of a rare blood group is positive; if electrophoresis shows only an internal control strip emerges, the detection result of the rare blood group is negative; and if electrophoresis shows no strip, the detection fails.

The rare blood group strip is: the strip at a location corresponding to the size of rare blood group amplification produce fragments after the rare blood group sample is amplified by a corresponding specific primer. The internal control strip is: the strip at a location corresponding to the size of internal control amplification product fragments after the blood sample to be tested is amplified by a corresponding internal control primer.

Most preferably, for the multiplex PCR reaction system with the specific primer sequences of SEQ ID NO: 1-6, sequences of the internal control primers thereof are SEQ ID NO: 17-18; for the multiplex PCR reaction system with the specific primer sequence of SEQ ID NO: 7-12, sequences of the internal control primers thereof are SEQ ID NO: 19-20; and for the multiplex PCR reaction system with the specific primer sequence of SEQ ID NO: 13-16, sequences of the internal control primers thereof are SEQ ID NO: 21-22.

More preferably, primer sequences of the Yt-K-Kpc system, the Dia-OK-Cob system and the Fyb-S system are as follows:

| Rare blood group system | Name of primer | Sequence | Amplification product (bp) | SNP loci |
|---|---|---|---|---|
| Yt-K-Kp c group system | Yt-Sm4 | TCATCAACGCGGGAGACTTAA (SEQ ID NO: 1) | 636 | Yt$^b$ |
| | Yt-as | CACGGGGCACACGACATT (SEQ ID NO: 2) | | |
| | K-sm5 | CTTCCTTAAACTTTAACCGCAT (SEQ ID NO: 3) | 204 | K |
| | K-as | CCCAACCTGCAACCTTCCTC (SEQ ID NO: 4) | | |
| | Kpc-sm2 | TGTCAATCTCCATCACTTCAAA (SEQ ID NO: 5) | 462 | Kp$^c$ |
| | Kpc-as | TCCTCCACCAGTTGTGACAT (SEQ ID NO: 6) | | |
| | Bactin-s | TTCCCTCCTCAGATCATTGCT (SEQ ID NO: 17) | 320 | Beta-act in (Reference) |
| | Bactin-as | TCACCTTCACCGTTCCAGTTT (SEQ ID NO: 18) | | |
| | dia-sm4h | GTGGGTGGTGAAGTCCAATCT (SEQ ID NO: 7) | 645 | Di$^a$ |
| Dia-OK- | dia-as | AGAGGGTCTGGCTGTCTTGAA (SEQ ID NO: 8) | | |

| Rare blood group system | Name of primer | Sequence | Amplification product (bp) | SNP loci |
|---|---|---|---|---|
| Cob group system | OK-sm8h | TACTCCTGCGTCTTCCTCAACA (SEQ ID NO: 9) | 292 | OK 274A |
| | OK-as | CTCCCCCTCGTTGATGTGTTC (SEQ ID NO: 10) | | |
| Fyb-S group system | co-smh | GGTGGGGAACAACCAGAGCGT (SEQ ID NO: 11) | 395 | Co$^b$ |
| | Co-ash | CCTCCAGCAACCTCTTGTCCTCTC (SEQ ID NO: 12) | | |
| | Beta-actinF | CGGCATCGTCACCAACTG (SEQ ID NO: 19) | 508 | Beta-actin (Reference) |
| | Beta-actinR | TGCAAAGAACACGGCTAAG (SEQ ID NO: 20) | | |
| | FYBS | CTTCCCAGATGGAGACTATCA (SEQ ID NO: 13) | 558 | Fy$^b$ |
| | FYBAS | AACAAGACAAAGATGGCAAGA (SEQ ID NO: 14) | | |
| | S-s | TGATAGCCGCATGACCCTTCT (SEQ ID NO: 15) | 442 | S |
| | S-asm | ACGATGGACAAGTTGTCCGA (SEQ ID NO: 16) | | |
| | Bactin-S2 | CTCTGCCTGACATGAGGGTTA (SEQ ID NO: 21) | 675 | Beta-actin (Reference) |
| | Bactin-AS | TCACCTTCACCGTTCCAGTTT (SEQ ID NO: 22) | | |

Note: The underlined parts represent specific SNP loci to be detected, and the boxes represent mismatch base introduced in the design of primers.

Preferably, the amount of components of the Yt-K-Kpc system, the Dia-OK-Cob system and the Fyb-S system can refer to the conventional multiplex PCR system. More preferably, TaKaRa Taq™ Hot Start Version, Cat.#R007A/B (Supplied with 10×PCR Buffer (Mg2+plus) and dNTP Mixture) are used, which is specifically as follows:

(1) Yt-K-Kpc System

| Name | Amount (μL/25 μL) |
|---|---|
| DNA template | 4 |
| Buffer | 2.5 |
| dNTP | 2 |
| Yt-sm4 | 1.75 |
| Yt-as | 1.75 |
| K-sm5 | 1 |
| K-as | 1 |
| Kpc-sm2 | 1 |
| Kpc-as | 1 |
| Bactin-s | 0.2 |
| Bactin-as | 0.2 |
| Tap-HS | 0.125 |
| H$_2$O | 8.475 |

(2) Dia-OK-Cob System

| Name | Amount (μL/25 μL) |
|---|---|
| DNA template | 4 |
| Buffer | 2.5 |
| dNTP | 2 |
| dia-sm4h | 1.75 |
| dia-as | 1.75 |
| OK-sm8h | 1 |
| OK-as | 1 |
| Co-smh | 1 |
| Co-ash | 1 |
| Beta-actinF | 0.2 |
| Beta-actinR | 0.2 |
| Tap-HS | 0.125 |
| H$_2$O | 8.475 |

(3) Fyb-S System

| Name | Amount (μL/25 μL) |
|---|---|
| DNA template | 4 |
| Buffer | 2.5 |
| dNTP | 2 |
| FYB-s | 0.75 |
| FYB-as | 0.75 |
| S-asm | 1 |
| S-s | 1 |
| Bactin-S2 | 0.2 |
| Bactin-as | 0.2 |
| Tap-HS | 0.125 |
| H$_2$O | 12.475 |

Preferably, the multiplex PCR amplification procedure of the Yt-K-Kpc system, the Dia-OK-Cob system and the Fyb-S system is as follows:

(1) Yt-K-Kpc System

| Phase | Step | Temperature (°C.) | Holding time | Cycles |
|---|---|---|---|---|
| First phase | 1 | 94 | 5 min | 1 |
| Second phase | 1 | 94 | 30 s | 5 |
| | 2 | 61 | 30 s | |
| | 3 | 72 | 45 s | |
| Third phase | 1 | 94 | 30 s | 30 |
| | 2 | 58 | 30 s | |

-continued

| Phase | Step | Temperature(° C.) | Holding time | Cycles |
|---|---|---|---|---|
| | 3 | 72 | 45 s | |
| Fourth phase | 1 | 72 | 7 min | 1 |

(2) Dia-OK-Cob System

| Phase | Step | Temperature (° C.) | Holding time | Cycles |
|---|---|---|---|---|
| First phase | 1 | 94 | 5 min | 1 |
| Second phase | 1 | 94 | 30 s | |
| | 2 | 60 | 30 s | 35 |
| | 3 | 72 | 45 s | |
| Third phase | 1 | 72 | 7 min | 1 |

(3) Fyb-S System

| Phase | Step | Temperature (° C.) | Holding time | Cycles |
|---|---|---|---|---|
| First phase | 1 | 94 | 5 min | 1 |
| Second phase | 1 | 94 | 30 s | |
| | 2 | 58 | 30 s | 35 |
| | 3 | 72 | 45 s | |
| Third phase | 1 | 72 | 7 min | 1 |

Preferably, in step 5), the weight percentage of the agarose used in electrophoresis is 2% agarose gel.

Analysis of detection results: the results are judged according to presence or absence and the size of the PCR product, if the gel imaging result of the sample shows that a strip emerges at a location corresponding to the size of a certain rare blood group PCR amplification product, or a location corresponding to the positive control amplification product, the rare blood group detection result of the sample is positive, and it indicates the blood sample may be a rare blood group or heterozygote having rare blood group SNP loci, which is further verified through molecular biology methods or serological methods; if the gel imaging result of the sample shows that no strip emerges at a location corresponding to the size of a certain rare blood group PCR amplification product, or a location corresponding to the positive control amplification product, it indicates that the rare blood group detection result of the sample is negative, that is, the blood sample does not belong to any one of Yt(b+), K, Kp(c+), Di(a+), Ok(a−), Co(b+), Fy(b+) and S blood groups.

A second aspect of the present invention discloses a rare blood multiplex PCR detection kit, wherein the kit includes multiple pairs of specific primers, and sequences of the multiple pairs of specific primers are SEQ ID NO: 1-6 and/or SEQ ID NO: 7-12 and/or SEQ ID NO: 13-16.

The rare blood multiplex PCR detection kit according to the present invention is detection for a Yt-K-Kpc system and/or a Dia-OK-Cob system and/or an Fyb-S system.

Preferably, the kit further includes one or more of PCR buffer solution, dNTP, Taq enzyme and ddH$_2$O.

Preferably, the kit further includes internal control primers, and if sequences of the multiplex pairs of specific primers are SEQ ID NO: 1-6, sequences of internal control primers corresponding thereto are SEQ ID NO: 17-18; if sequences of the multiplex pairs of specific primers are SEQ ID NO: 7-12, sequences of internal control primers corresponding thereto are SEQ ID NO: 19-20; and if sequences of the multiplex pairs of specific primers are SEQ ID NO: 13-16, sequences of internal control primers corresponding thereto are SEQ ID NO: 21-22.

Preferably, the kit further includes a positive control. The positive control is the plasmid containing a rare blood group SNP loci gene fragment, and the positive control is capable of being amplified by a pair of specific primers in the multiplex pairs of specific primers with sequences of SEQ ID NO: 1-16.

A third aspect of the present invention provides a rare blood group rapid screening method, which detects multiple blood samples in a single PCR tube under one PCR procedure on the basis of the multiplex PCR detection method of the present invention.

Efficient screening of rare blood groups is achieved through a combination of a multiplex PCR method and a Pool detection scheme.

The design principle that the rare blood group screening method of the present invention combines the multiplex PCR method with the Pool detection scheme is as follows: the multiplex PCR method can amplify specific sequences of rare blood group antigens through specific primers thereof, to judge whether SNP loci of a certain rare blood group are included by observing whether a strip emerges in gel imaging; the Pool detection scheme can mix a certain number of blood samples for detection, if the multiplex PCR detection result of mixed samples shows that detection of rare blood group antigen SNP loci is positive, resolve the Pool, to perform multiplex PCR detection respectively, and then continue resolve the Pool whose detection result is positive, until the original positive sample has been determined; finally, verify the detected samples containing rare blood group SNP loci through PCR-SSP or sequencing or serology methods.

Preferably, the rare blood group screening method of the present invention specifically includes:

A. preparing a sample to be tested: building a Pool with multiplex blood samples, respectively extracting DNA templates of the blood samples forming the Pool, and mixing the DNA templates, to obtain a sample to be tested of the Pool;

B. screening out positive Pool: using step 2) to step 6) of the said multiplex PCR detection method according to the present invention, to perform multiplex PCR detection on the sample to be tested of the Pool obtained in step A, and screening out Pool whose detection result is positive;

C. detection and resolution of positive Pool is selected from any one of the following:

a) if the number of blood samples in the Pool whose detection result is positive is less than or equal to 5, taking the DNA templates of the blood samples in the Pool as a sample to be tested respectively, using step 2) to step 6) of the multiplex PCR detection method according to the present invention to perform multiplex PCR detection, and screening out blood samples whose detection result is positive;

b) if the number of blood samples in the Pool whose detection result is positive is greater than 5, resolving the blood samples of the Pool screened out in step B whose detection result is positive, to form two new Pools, respectively mixing DNA templates of the blood samples of the two Pools, to obtain samples to be tested of the two Pools, and using step 2) to step 6) of the multiplex PCR detection method according to the present invention to perform multiplex PCR detection, to screen out the Pool whose detection result is positive; and D. repeating step C.

Preferably, the multiplex blood samples according to the present invention mean that the number of the blood samples is 2-12. More preferably, the multiplex blood samples mean that the number of the blood samples is 5-12. Most preferably, the multiplex blood samples mean that the number of the blood samples is 5.

The screening method performs detection after making multiplex blood samples forming a Pool, and if the multiplex PCR result is not positive, all the blood samples forming the Pool do not belong to the rare blood group; if the multiplex PCR result is positive, at least one blood sample in the samples forming the Pool contains rare blood group SNP loci. Thus, rare blood group detection is continuously performed on the Pool whose detection result is positive: when the number of the blood samples of the positive Pool is more (greater than 5), resolve the Pool and perform detection respectively, until the number of the blood samples of the positive Pool is less than or equal to 5, take DNA templates of the blood samples forming the Pool as samples to be tested to perform multiplex PCR reaction, to screen out blood samples whose blood detection is positive; when the number of the blood samples of the positive Pool is less (less than or equal to 5), DNA templates of the blood samples in the Pool can be taken as samples to be tested respectively to perform multiplex PCR reaction, to screen out blood samples whose blood detection is positive. Finally, confirm blood samples which are positive through biological methods, serological methods or sequencing.

A fourth aspect of the present invention provides a human rare blood group multiplex PCR detection method, a kit using the multiplex PCR detection method for detection, and application of a rapid screening method based on the multiplex PCR detection method in human rare blood group detection and rapid screening.

The beneficial effects of the present invention are as follows: the rare blood group is caused by polymorphism of blood cell surface antigen SNP loci, and thus, as the primers used in the rare blood group detection in the prior art are designed with respect to SNP loci of high-frequency antigens (common blood group antigens), negative results are detectable in the prior art (non-rare blood group samples have strips at a corresponding location in the gel through PCR amplification and gel imaging tests; while the rare blood group has no strips); the present invention take the advantage of special design of primers amplifying alleles containing low-frequency antigen (rare blood group antigen) SNP loci or alleles containing high-frequency antigen deletion phenotype SNP loci to make rare blood group detection is positive being detectable, so that the multiplex PCR method can be combined with the Pool detection scheme: on the one hand, the multiplex PCR can perform typing on multiplex target antigen genes in the same PCR reaction at the same time through multiplex pairs of primers with respect to different rare blood group SNP loci, more information is obtained in a single reaction, the PCR method has good repetition, high sensitivity, and strong specificity, which can form commercial detection reagents, and is more cost-effective; on the other hand, the defect that the existing detection method only detects a blood sample once, and is inefficient and time-consuming is overcome through the detection scheme of mixing multiple blood samples into a Pool detection pool, which can one-time detect multiple blood samples, and improves the detection efficiency. Moreover, the present invention overcomes the problem that the blood samples have too many fragments to be tested and interfere with multiplex PCR through designing mismatched primers and optimization of different primers on combinations, which can perform screening of high sensitivity and strong specificity on the rare blood group. Therefore, the detection method of the present invention combines the advantages of the multiplex PCR method and the Pool detection scheme, which has a multiplying effect, greatly improves the detection efficiency of rare blood group, improves the detection sensitivity and specificity, shortens the time to be spent on the detection, reduces the detection costs, and is of great practical significance.

DETAILED DESCRIPTION OF THE PREFERRED EMBODIMENTS

Figure 1:
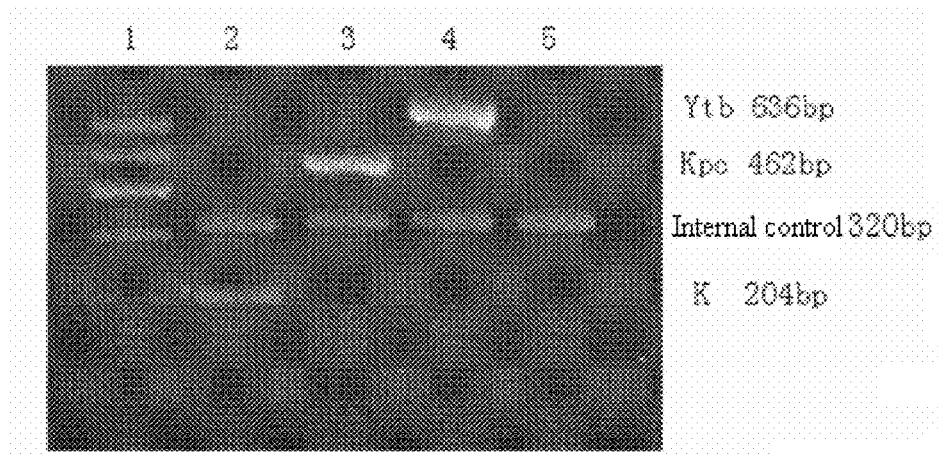
FIG. 1 illustrates gel imaging results of amplification products of a Yt-K-Kpc system.

The following are specific embodiments of the present invention. The embodiments are only for describing the present invention, but not for limiting the scope of the present invention.

Embodiment 1 Primer Construction

Primer design principle: design PCR-SSP primer 3' end bases to be aiming at a rare blood group antigen allele-specific locus (an amplification locus in the literature is a normal antigen allele-specific locus), and introduce a small amount of mismatch into specific primers.

I. Sequences that primer design refers to are as follows:
Yt-K-Kpc System:
*Homo sapiens* acetylcholinesterase (ACHE), RefSeqGene on chromosome 7 (NCBI Reference Sequence: NG_007474.1)
*Homo sapiens* Kell blood group, metallo-endopeptidase (KEL), RefSeqGene on chromosome 7 (NCBI Reference Sequence: NG_007492.1)
Dia-OK-Cob System:
*Homo sapiens* solute carrier family 4, anion exchanger, member 1 (erythrocyte membrane protein band 3, Diego blood group) (SLC4A1), RefSeqGene on chromosome 17 (NCBI Reference Sequence: NG_007498.1)
*Homo sapiens* basigin (Ok blood group) (BSG), RefSeqGene on chromosome 19 (NCBI Reference Sequence: NG_007468.1)
*Homo sapiens* aquaporin 1 (Colton blood group) (AQP1), RefSeqGene on chromosome 7 (NCBI Reference Sequence: NG_007475.1)
Fyb-S System:

*Homo Sapiens* Duffy blood group, chemoline receptor (DARC), RefSeqGene on Chromosome 1. (NCBI Reference Sequence: NG_011626.1)

*Homo sapiens* glycophorin B (MNS blood group) (GYPB), RefSeqGene on chromosome 4. (NCBI Reference Sequence: NG_007483.2)

Primers are synthesized with a conventional method.

II. A Yt-K-Kpc multiplex PCR reaction system is specifically as follows:

(1) PCR Primer Sequence

| Name of Primer | Sequence | Size of amplification product (bp) | SNP loci |
|---|---|---|---|
| Yt-sm4 | TCATCAACGCGGGAGACTTAA (SEQ ID NO: 1) | 636 | $Yt^b$ |
| Yt-as | CACGGGGCACACGACATT (SEQ ID NO: 2) | | |
| K-sm5 | CTTCCTTAAACTTTAACCGCAT (SEQ ID NO: 3) | 204 | K |
| K-as | CCCAACCTGCAACCTTCCTC (SEQ ID NO: 4) | | |
| Kpc-sm2 | TGTCAATCTCCATCACTTCAAA (SEQ ID NO: 5) | 462 | $Kp^c$ |
| Kpc-as | TCCTCCACCAGTTGTGACAT (SEQ ID NO: 6) | | |
| Bactin-s | TTCCCTCCTCAGATCATTGCT (SEQ ID NO: 17) | 320 | Beta-actin (reference) |
| Bactin-as | TCACCTTCACCGTTCCAGTTT (SEQ ID NO: 18) | | |

(2) System Composition

The multiplex PCR system in the present invention uses TaKaRa Taq™ Hot Start Version, Cat.#R007A/B (Supplied with 10×PCR Buffer ($Mg^{2+}$ plus) and dNTP Mixture), the total volume of the system is 25 μL, and the system composition is specifically as follows:

| Name | Volume (μL) |
|---|---|
| DNA template | 4 |
| Buffer | 2.5 |
| dNTP | 2 |
| Yt-sm4 | 1.75 |
| Yt-as | 1.75 |
| K-sm5 | 1 |
| K-as | 1 |
| Kpc-sm2 | 1 |
| Kpc-as | 1 |
| Bactin-s | 0.2 |
| Bactin-as | 0.2 |
| Tap-HS | 0.125 |
| $H_2O$ | 8.475 |

(3) PCR Amplification Procedure:

| Phase | Step | Temperature(° C.) | Holding time | Cycles |
|---|---|---|---|---|
| First phase | 1 | 94 | 5 min | 1 |
| Second phase | 1 | 94 | 30 s | 5 |
| | 2 | 61 | 30 s | |
| | 3 | 72 | 45 s | |
| Third phase | 1 | 94 | 30 s | 30 |
| | 2 | 58 | 30 s | |
| | 3 | 72 | 45 s | |
| Fourth phase | 1 | 72 | 7 min | 1 |

III. A Dia-OK-Cob multiplex PCR reaction system is specifically as follows:

(1) PCR Primer Sequence

| Name of primer | Sequence | Size of amplification product (bp) | SNP loci |
|---|---|---|---|
| dia-sm4b | GTGGGTGGTGAAGTCCAATCT (SEQ ID NO: 7) | 645 | $Di^a$ |
| dia-as | AGAGGGTGTGGCTGTCTTGAA (SEQ ID NO: 8) | | |
| OK-sm8b | TACTCCTGCGTCTTCCTCAACA (SEQ ID NO: 9) | 292 | OK 274A |
| OK-as | CTCCCCCTCGTTGATGTGTTC (SEQ ID NO: 10) | | |
| Co-smh | GGTGGGGAACAACCAGAGCGT (SEQ ID NO: 11) | 395 | $Co^b$ |

| Name of primer | Sequence | Size of amplification product (bp) | SNP loci |
|---|---|---|---|
| Co-ash | CCTCCAGCAACCTCTTGTCCTCTC (SEQ ID NO: 12) | | |
| Beta-actinF | CGGCATCGTCACCAACTG (SEQ ID NO: 19) | 508 | Beta-actin |
| Beta-actinR | TGCAAAGAACACGGCTAAG (SEQ ID NO: 20) | | (reference) |

(2) System Composition

The multiplex PCR system in the present invention uses TaKaRa Taq™ Hot Start Version, Cat.#R007A/B (Supplied with 10×PCR Buffer (Mg$^{2+}$ plus) and dNTP Mixture), the total volume of the system is 25 μL, and the system composition is specifically as follows:

| Name | Volume (μL) |
|---|---|
| DNA template | 4 |
| Buffer | 2.5 |
| dNTP | 2 |
| dia-sm4h | 1.75 |
| dia-as | 1.75 |
| OK-sm8h | 1 |
| OK-as | 1 |
| Co-smh | 1 |
| Co-ash | 1 |
| Beta-actinF | 0.2 |
| Beta-actinR | 0.2 |
| Tap-HS | 0.125 |
| H$_2$O | 8.475 |

(3) PCR Amplification Procedure:

| Phase | Step | Temperature (° C.) | Holding time | Cycles |
|---|---|---|---|---|
| First phase | 1 | 94 | 5 min | 1 |
| Second phase | 1 | 94 | 30 s | |
| | 2 | 60 | 30 s | 35 |
| | 3 | 72 | 45 s | |
| Third phase | 1 | 72 | 7 min | 1 |

IV. Fyb-S multiplex PCR reaction system is specifically as follows:

(1) PCR Primer Sequence

| Name of primer | Sequence | Size of amplification product (bp) | SNP loci |
|---|---|---|---|
| FYBS | CTTCCCAGATGGAGACTATCA (SEQ ID NO: 13) | 558 | Fy$^b$ |
| FYBAS | AACAAGACAAAGATGGCAAGA (SEQ ID NO: 14) | | |
| S-s | TGATAGCCGCATGACCCTTCT (SEQ ID NO: 15) | 442 | S |
| S-asm | ACGATGGACAAGTTGTCCGA (SEQ ID NO: 16) | | |
| Bactin-S2 | CTCTGCCTGACATGAGGGTTA (SEQ ID NO: 21) | 675 | Beta-actin |
| Bactin-AS | TCACCTTCACCGTTCCAGTTT (SEQ ID NO: 22) | | (reference) |

(2) System Composition

The multiplex PCR system in the present invention uses TaKaRa Taq™ Hot Start Version, Cat.#R007A/B (Supplied with 10×PCR Buffer (Mg$^{2+}$ plus) and dNTP Mixture), the total volume of the system is 25 μL, and the system composition is specifically as follows:

| Name | Volume (μL) |
|---|---|
| DNA template | 4 |
| Buffer | 2.5 |
| dNTP | 2 |
| FYB-s | 0.75 |
| FYB-as | 0.75 |
| S-asm | 1 |
| S-s | 1 |
| Bactin-S2 | 0.2 |
| Bactin-as | 0.2 |
| Tap-HS | 0.125 |
| H$_2$O | 12.475 |

(3) PCR Amplification Procedure:

| Phase | Step | Temperature (° C.) | Holding time | Cycles |
|---|---|---|---|---|
| First phase | 1 | 94 | 5 min | 1 |
| Second phase | 1 | 94 | 30 s | |
| | 2 | 58 | 30 s | 35 |
| | 3 | 72 | 45 s | |
| Third phase | 1 | 72 | 7 min | 1 |

Embodiment 2 Construction of Positive Control

Method I: DNA samples from rare blood group donors were obtained, then amplified by primers designed to amplify the fragments containing SNP loci to be detected. The amplification products were connected to a pGM-T vector, subsequently transformed into DH5α competent cells. The positive monoclonal colonies were picked to be identified by sequencing. Thus the Ytb, K, Dia and Cob positive controls were constructed.

1. Design primers

| Blood group | Name of primer | Sequence |
|---|---|---|
| Ytb | Ytb-F | TCCTCCTTGGACGTGTACGAT (SEQ ID NO: 23) |
| | Ytb-R | CTCCTCTGCCGTGTAGTTTCG (SEQ ID NO: 24) |
| K | K-F | TTATGCCAGAATCAGGTTAGA (SEQ ID NO: 25) |
| | K-R | GAGAGAAGGAATGTACGGGAG (SEQ ID NO: 26) |
| Dia | Dia-F | CAAGCCACCCAAGTATCACCC (SEQ ID NO: 27) |
| | Dia-R | CATCCCGACCTTCCTCCTCAT (SEQ ID NO: 28) |
| Cob | Cob-F | AAAGCCTATTAGAGCAACGG (SEQ ID NO: 29) |
| | Cob-R | CCTAGAGGTGGTTTATTTGGA (SEQ ID NO: 30) |
| Fyb | Fyb-F | AGAGTCCCTTATCCCTATGCC (SEQ ID NO: 31) |
| | Fyb-R | ACCTCACCAGGAAATCCAGTC (SEQ ID NO: 32) |
| S | S-F | GCACAGGTGGAACAGTAAGG (SEQ ID NO: 33) |
| | S-R | GGTTGTCAAGATGGTCCCTAA (SEQ ID NO: 34) |

2. Amplification system (1) Ytb, K, Dia, Cob

| Name | Volume (μL) |
|---|---|
| DNA template | 2.5 |
| Buffer | 5 |
| dNTP | 4 |
| Upstream primer | 1.75 |
| Downstream primer | 1.75 |
| Tap-HS | 0.25* |
| H₂O | 34.75 |

*TaKaRa TaqTM Hot Start Version, Cat.#R007A/B (supplied with 10 × PCR Buffer (Mg2+plus) and dNTP Mixture)

(2) Fyb, S

| Name | Volume (μL) |
|---|---|
| DNA template | 2.5 |
| Buffer | 5 |
| dNTP | 4 |
| Upstream primer | 2 |
| Downstream primer | 2 |
| Tap-HS | 0.25* |
| H₂O | 34.75 |

*TaKaRa TaqTM Hot Start Version, Cat.#R007A/B (Supplied with 10 × PCR Buffer (Mg2+ plus) and dNTP Mixture)

3. PCR amplification procedure (1) Ytb Amplification Procedure

| Phase | Step | Temperature (° C.) | Holding time | Cycles |
|---|---|---|---|---|
| First phase | 1 | 94 | 5 min | 1 |
| Second phase | 1 | 94 | 1 min | 38 |
| | 2 | 60 | 1 min | |
| | 3 | 72 | 1.5 min | |
| Third phase | 1 | 72 | 7 min | 1 |

(2) K Amplification Procedure

| Phase | Step | Temperature(° C.) | Holding time | Cycles |
|---|---|---|---|---|
| First phase | 1 | 94 | 5 min | 1 |
| Second phase | 1 | 94 | 1 min | 38 |
| | 2 | 55 | 1 min | |
| | 3 | 72 | 1.5 min | |
| Third phase | 1 | 72 | 7 min | 1 |

(3) Dia Amplification Procedure

| Phase | Step | Temperature (° C.) | Holding time | Cycles |
|---|---|---|---|---|
| First phase | 1 | 94 | 5 min | 1 |
| Second phase | 1 | 94 | 40 s | 38 |
| | 2 | 60 | 40 s | |
| | 3 | 72 | 1 min | |
| Third phase | 1 | 72 | 7 min | 1 |

(4) Cob Amplification Procedure

| Phase | Step | Temperature (° C.) | Holding time | Cycles |
|---|---|---|---|---|
| First phase | 1 | 94 | 5 min | 1 |
| Second phase | 1 | 94 | 1 min | 38 |
| | 2 | 57 | 1 min | |
| | 3 | 72 | 1.5 min | |
| Third phase | 1 | 72 | 7 min | 1 |

(5) Fyb Amplification Procedure

| Phase | Step | Temperature (° C.) | Holding time | Cycles |
|---|---|---|---|---|
| First phase | 1 | 94 | 5 min | 1 |
| Second phase | 1 | 94 | 1 min | 35 |
| | 2 | 57 | 1 min | |
| | 3 | 72 | 1 min 30 s | |
| Third phase | 1 | 72 | 7 min | 1 |

(6) S Amplification Procedure

| Phase | Step | Temperature (° C.) | Holding time | Cycles |
|---|---|---|---|---|
| First phase | 1 | 94 | 5 min | 1 |
| Second phase | 1 | 94 | 1 min | 35 |
| | 2 | 58 | 1 min | |
| | 3 | 72 | 1 min 30 s | |
| Third phase | 1 | 72 | 7 min | 1 |

4. The amplification products were purified by gel extraction kit, and connected to a pGM-T vector (purchased from TIANGEN BIOTECH), transformed into DH5α competent cells. The positive monoclonal colonies were picked to be identified by sequencing.

Method II. Use site-directed mutagenesis methods to construct Kpc, Ok positive control plasmids.

1. Construction of Kpc Control Plasmids

1) According to KEL (encode Kell blood group system kpc antigens, Gene bank sequence number NG07492) gene sequences in Genbank database, design that the primers are amplified with gene fragments containing SNP loci to be mutated.

Primer sequences are as follows:

(SEQ ID NO: 35)
Kpb-F GGTAAGATGGCACATGGACAAAGGC

```
                                        (SEQ ID NO: 36)
Kpb-R CTGCGGCGAACCTCTGCTTTAG
```

The amplification system is as follows:

| | |
|---|---|
| 10 × PCR Buffer (containing MgCl$_2$) | 5.0 µl |
| 5 mM dNTPs | 2.0 µl |
| 10 µM Kpb-F | 2.0 µl |
| 10 µM Kpb-R | 2.0 µl |
| DNA | 5.0 µl |
| Taq | 0.25 µl |
| H$_2$O | 33.75 µl |

The amplification procedure is as follows:

| Phase | Step | Temperature (° C.) | Holding time | Cycles |
|---|---|---|---|---|
| First phase | 1 | 95 | 2 min | 1 |
| | 1 | 94 | 30 s | |
| Second phase | 2 | 58 | 30 s | 35 |
| | 3 | 72 | 30 s | |
| Third phase | 1 | 72 | 10 min | 1 |

2) The amplification products were purified by gel extraction kit, and connected to a pGEM-T easy vector overnight at 4° C.

3) The ligation products are transformed into *E. coli* DH5α competent cells, coated on LB solid plates containing ampicillin and incubated at 37° C. overnight. To pick positive clones to be incubated in LB liquid culture medium containing ampicillin at 250r/min, 37° C. overnight, extract plasmids, and use T7 universal sequencing primers to sequence and analyze inserted fragments.

4) Design one mutagenic primer and another flanking primer (5' ends of two primers are adjacent to each other), take recombinant plasmids containing normal sequences of genes to be mutated as templates for amplification of full-length plasmids, and introduce mutation loci.

Primer sequences are as follows:

```
KPC MF mutagenic primer
                                        (SEQ ID No: 37)
TCACAGCTGTTCCAGTTTCT KPC MR flanking primer
                                        (SEQ ID NO: 38)
AGTGATGGAGTTGACAAGG
```

The amplification system is as follows:

| | |
|---|---|
| 10 × PCR buffer | 5.0 µl |
| 25 mM MgSO$_4$ | 2.0 µl |
| 2 mM dNTPs | 5.0 µl |
| 10 µM OK-Mu | 2 µl |
| 10 µM PGEMT-R | 2 µl |
| Recombinant plasmid template | 5.0 µl |
| KOD-Plus fidelity DNA polymerase | 1 µl |
| Fill deionized water to | 50 µl |

The amplification procedure is as follows:

| Phase | Step | Temperature (° C.) | Holding time | Cycles |
|---|---|---|---|---|
| First phase | 1 | 94 | 2 min | 1 |
| | 1 | 94 | 30 s | |
| Second phase | 2 | 60 | 30 s | 35 |
| | 3 | 68 | 4 min | |
| Third phase | 1 | 72 | 8 min | 1 |

5) Obtain detection controls of blood group antigen genes containing mutant SNP loci.

After purification by gel extraction kit, perform 5' end phosphorylation on the PCR products.

20 µl phosphorylation system:

| | |
|---|---|
| 10 × reaction buffer A | 2 µl |
| 10 mM ATP | 2 µl |
| T4 Polynucletide Kinase | 1 µl |
| PCR recovered product | 2 µl |
| ddH$_2$O | 13 µl |

Perform self-ligation after phosphorylation, and 10 µl ligation system is as follows:

| | |
|---|---|
| Phosphorylated product | 2 µl |
| 2 × Rapid Ligation Buffer | 5 µl |
| T4 DNA Ligase | 1 µl |
| ddH$_2$O | 2 µl |

The ligation is performed at 4 overnight. Transform the ligation products into the DH5α competent cells, incubate at 37 overnight, and then extract plasmids, and use the T7 sequencing primers to sequence and analyze results of the mutation.

2. Construction of Ok Control Plasmids

1) According to BSG (encode OK blood group system Ok$^a$ antigens, Gene bank sequence number NG07468) gene sequences in Genbank database, design that the primers are amplified with gene fragments containing SNP loci to be mutated.

Primer sequences are as follows:

```
                                        (SEQ ID NO: 39)
OKa-F GACTGGGACAGTTTTGCTTTTTCAC (SEQ ID NO: 40)
OKa-R GTCTCCCCCTCGTTGATGTGTTCTG
```

The amplification system is as follows:

| | |
|---|---|
| 10 × PCR Buffer | 5.0 µl |
| MgCl2 | 2.5 µl |
| 5 mM dNTPs | 2.0 µl |
| 10 µM OKa-F | 2.0 µl |
| 10 µM OKa-R | 2.0 µl |
| DNA | 5.0 µl |
| Taq | 0.4 µl |
| H$_2$O | 50 µl |

The amplification procedure is as follows:

| Phase | Step | Temperature (° C.) | Holding time | Cycles |
|---|---|---|---|---|
| First phase | 1 | 95 | 10 min | 1 |
| | 1 | 94 | 40 s | |
| Second phase | 2 | 61 | 40 s | 35 |
| | 3 | 72 | 1 min | |

| Phase | Step | Temperature (° C.) | Holding time | Cycles |
|---|---|---|---|---|
| Third phase | 1 | 72 | 5 min | 1 |

2) The amplification products were purified by gel extraction kit, and connected to a pGEM-T easy vector overnight at 4° C.

3) The ligation products are transformed into E. coli DH5α competent cells, coated on LB solid plates containing ampicillin and incubated at 37° C. overnight. To pick positive clones to be incubated in LB liquid culture medium containing ampicillin at 250r/min, 37° C. overnight, extract plasmids, and use T7 universal sequencing primers to sequence and analyze inserted fragments.

4) Design one mutagenic primer and another flanking primer (5' ends of two primers are adjacent to each other), take recombinant plasmids containing normal sequences of genes to be mutated as templates for amplification of full-length plasmids, and introduce mutation loci.

Primer sequences are as follows:

```
                                         (SEQ ID No: 41)
OKa-Mu mutagenic primer CATGGGCTTGGGGAGGAAGAC (SEQ ID No: 42)
PGEMT-R flanking primer GGCACGGCCAACATCCAGCTC
```

The amplification system is as follows:

| 10 × PCR buffer | 5.0 µl |
|---|---|
| 25 mM MgSO₄ | 2.0 µl |
| 2 mM dNTPs | 5.0 µl |
| 10 µM OK-Mu | 2 µl |
| 10 µM PGEMT-R | 2 µl |
| Recombinant plasmid template | 5.0 µl |
| KOD-Plus fidelity DNA polymerase | 1 µl |
| Fill deionized water to | 50 µl |

The amplification procedure is as follows:

| Phase | Step | Temperature (° C.) | Holding time | Cycles |
|---|---|---|---|---|
| First phase | 1 | 94 | 10 min | 1 |
| Second phase | 1 | 94 | 30 s | 35 |
| | 2 | 60 | 30 s | |
| | 3 | 68 | 4 min | |
| Third phase | 1 | 72 | 5 min | 1 |

5) Obtain detection controls of blood group antigen genes containing mutant SNP loci.

After purification by gel extraction kit, perform 5' end phosphorylation on the PCR products.

20 µl phosphorylation system:

| 10 × reaction buffer A | 2 µl |
|---|---|
| 10 mM ATP | 2 µl |
| T4 Polynucletide Kinase | 1 µl |
| PCR recovered product | 2 µl |
| ddH₂O | 13 µl |

Perform self-ligation after phosphorylation, and 10 µl ligation system is as follows:

| Phosphorylated product | 2 µl |
|---|---|
| 2 × Rapid Ligation Buffer | 5 µl |
| T4 DNA Ligase | 1 µl |
| ddH₂O | 2 µl |

The ligation is performed at 4 overnight. Transform the ligation products into the DH5α competent cells, incubate at 37 overnight, and then extract plasmids, and use the T7 sequencing primers to sequence and analyze results of the mutation.

Embodiment 3 Screening of Rare Blood Group

In the following experiments, non-rare blood group blood samples, rare blood group blood samples, and control plasmids are all verified by sequencing.

I. Detection of Pool of Blood Samples not Containing Rare Blood Groups Specific SNP Loci Randomly collect 12 blood samples, respectively extract genomic DNA, and sequence to verify not containing rare blood groups specific SNP loci.

Rare blood group detection using the rare blood group screening method in the present invention: mixing the obtained DNA templates, to form a sample to be tested containing 12 blood samples; respectively add the samples to be tested into the corresponding multiplex PCR reaction system in Embodiment 1, to obtain PCR reaction solutions of the Yt-K-Kpc system, the Dia-OK-Cob system and the Fyb-S system, and prepare a PCR reaction solutions of the positive control at the same time; perform amplification reaction on the PCR reaction solutions obtained in the previous step according to corresponding PCR amplification procedures; detect the obtained amplification products in the agarose gel by electrophoresis, and observe results through a gel imager.

The gel imager shows that an internal control strip emerges, but no strip emerges at a location corresponding to the size of the positive control amplification fragment, and thus the detection result of the rare blood group screening method is that the 12 blood samples do not have rare blood group blood samples, and the detection result is consistent with the DNA sequencing result.

II. Detection of Pool of Blood Samples Containing Rare Blood Groups Specific SNP Loci Select 4 blood samples not containing rare blood groups specific SNP loci, extract DNA templates respectively, and mix the templates, after mixing, the mixed templates form with a blood sample genome DNA not containing rare blood groups specific SNP loci, a Yt(b+) blood sample genome DNA, a K blood sample genome DNA, and Kpc control plasmids respectively to obtain four Pools each containing 5 DNA samples, perform amplification according to the Yt-K-Kpc system in Embodiment 1 and the corresponding reaction condition, and the amplification products are detected by the gel imager after gel electrophoresis.

Please refer to FIG. 1 of the specification for electrophoresis results. Lane 1: Marker, fragments are 100, 200, 300, 400, 500, 600 bp; Lane 2, 3, 4: four 3.2 µl mixtures of blood sample genome DNA not containing rare blood groups specific SNP loci (concentration of 50-100 ng/µl)+0.8 µl rare blood group genome DNA (concentration of 50-100 ng/µl)

or control plasmids (concentration of 0.01 ng/μl); Lane 5: five 4 μl blood sample genome DNAs not containing rare blood groups specific SNP loci (concentration of 50-100 ng/μl).

The gel imager shows that, lanes 2, 3, 4 have strips at locations corresponding to the sizes of the corresponding rare blood group amplification fragments, and detection results of Pools forming Lanes 2, 3, 4 are positive; as the number of DNA samples of Pools in Lanes 2, 4, 5 is equal to 5, DNAs of blood samples in the Pools of Lanes 2, 3, 4 are taken as templates for multiplex PCR reaction, and the rare blood group detection result obtained with the multiplex PCR method is consistent with the DNA sequencing result.

2. Dia-OK-Cob System

Select 4 genome DNAs of blood samples not containing rare blood groups specific SNP loci and mix them, after mixing, the mixed DNAs form with two genome DNA samples of blood samples not containing rare blood groups specific SNP loci, a Di(a+b+) blood sample genome DNA, OK control plasmids, a Co(b+) blood sample genome DNA respectively to obtain five Pools each containing 5 DNA samples, perform amplification according to the Dia-OK-Cob system in Embodiment 1 and the corresponding reaction condition, and the amplification products are detected by the gel imager after gel electrophoresis.

Figure 2:
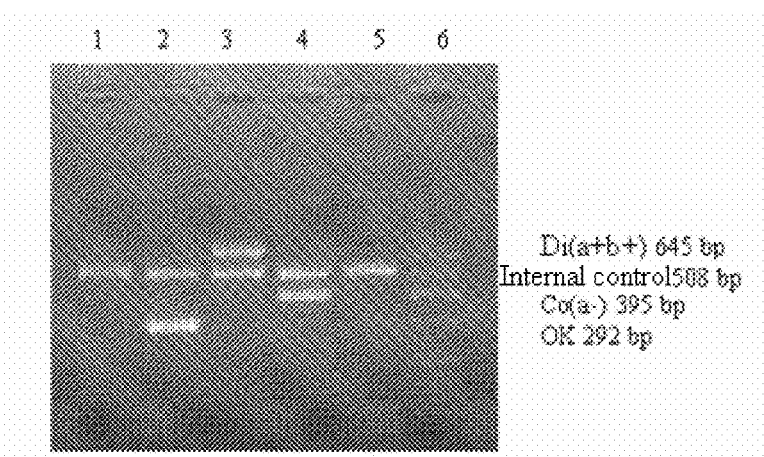
FIG. 2 illustrates gel imaging results of amplification products of a Dia-OK-Cob system.

Please refer to FIG. 2 of the specification for electrophoresis results. Lanes 1, 5: five 4 μl blood sample genome DNAs not containing rare blood groups specific SNP loci (concentration of 50-100 ng/μl); Lane 2, 3, 4: four 3.2 μl mixtures of blood sample genome DNA not containing rare blood groups specific SNP loci (concentration of 50-100 ng/μl)+0.8 μl rare blood group genome DNA (concentration of 50-100 ng/μl) or control plasmids (concentration of 0.01 ng/μl); Lane 6: Marker, fragments are 100, 200, 300, 400, 500, 600 bp.

The gel imager shows that, lanes 2, 3, 4 have strips at locations corresponding to the sizes of the corresponding rare blood group amplification fragments, and detection results of Pools forming Lanes 2, 3, 4 are positive; as the number of DNA samples of Pools in Lanes 2, 3, 4 is equal to 5, DNAs of blood samples in the Pools of Lanes 2, 3, 4 are taken as templates for multiplex PCR reaction, and the rare blood group detection result obtained with the multiplex PCR method is consistent with the DNA sequencing result.

3. Fyb-S System

A. Select 4 genome DNAs of specific SNP loci blood samples not containing rare blood groups and mix them, after mixing, the mixed DNAs form with a genome DNA of blood samples not containing rare blood groups specific SNP loci, a Fy(a+b+) blood sample genome DNA and an S+s− blood sample genome DNA respectively to obtain three Pools each containing 5 DNA samples.

B. Select 3 genome DNAs of blood samples not containing rare blood groups specific SNP loci and mix them, and after mixing, add the mixed DNAs to a Fy(a+b+) blood sample genome DNA and an S+s− blood sample genome DNA, to form a Pool containing 5 DNA samples.

Perform amplification according to the Fyb-S system in Embodiment 1 and the corresponding reaction condition, and the amplification products are detected by the gel imager after gel electrophoresis.

Figure 3:
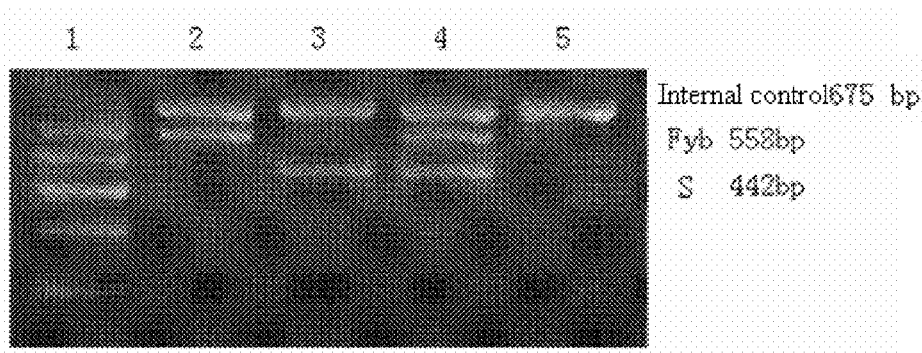
FIG. 3 illustrates gel imaging results of amplification products of an Fyb-S system.

Please refer to FIG. 3 of the specification for electrophoresis results. The gel imager shows that, lanes 2, 3 have strips at locations corresponding to the sizes of the corresponding rare blood group amplification fragments, and detection results of Pools forming Lanes 2, 3 are positive; lane 4 has strips at locations corresponding to Fyb and S, detection results of Pool of Lane 4 containing rare blood groups of Fyb and S are positive; DNAs of blood samples in the Pools of Lanes 2, 3, 4 are taken as templates for multiplex PCR reaction, and the rare blood group detection result obtained with the multiplex PCR method is consistent with the DNA sequencing result.

Embodiment 4 Screening of Rare Blood Group Kit

In the following experiments, non-rare blood group blood samples, rare blood group blood samples, and control plasmids are all verified by sequencing.

1. Experimental Materials

Take out 11 blood samples of not containing rare blood groups specific SNP loci, respectively extract DNA templates, and mix the DNA templates of 11 blood samples; add a Fy(b+) blood sample genome DNA to the template DNA mixture, to prepare a Pool containing 12 DNA samples.

2. Experimental Methods

Take out 3 samples to be tested of the Pool, with reference to the Yt-K-Kpc system, the Dia-OK-Cob system and the Fyb-S system in Embodiment 1, and through PCR primers and other reagents in the kit, respectively prepare PCR reaction solutions of the three systems, and the PCR reaction solution of the positive control. Perform amplification reaction according to the amplification procedures of the Yt-K-Kpc system, the Dia-OK-Cob system and the Fyb-S system in Embodiment 1 respectively, place the amplification products in the agarose gel for electrophoresis, and observe results through a gel imager. The electrophoresis shows: amplification of the Yt-K-Kpc system and the Dia-OK-Cob system has no strips, it indicates that the blood samples of the Pool for detection do not belong to any one of Yt(b+), K, Kp(c+), Di(a+), Ok(a−) or Co(b+); amplification of the Fyb-S system has a strip, and the strip emerges at a location corresponding to a Fy(b+) blood group, and it proves that the Pool of the 12 blood samples may have a Fy(b+) blood group.

As the number of the blood samples in the Pool is 12 (greater than 5), the Pool is resolved into two new Pools each containing 6 blood samples, and multiplex PCR detection is performed according to the conditions of the Fyb-S system, to screen out Pools whose detection result is positive. Continue resolving the Pools whose detection result is positive, until the number of the blood samples in the Pools whose detection result is positive is 3, and multiplex PCR detection is performed on 3 DNA samples respectively, to finally detect the blood samples whose detection result is positive.

DNA sequencing is performed on the blood samples whose PCR result is positive, and the result shows that the sequencing result is consistent with the result of the human rare blood group multiplex PCR screening method.

Embodiment 5 Experiment of Screening Sensitivity of Rare Blood Group

1. Experimental methods: extract control plasmids, perform quantification with ultraviolet spectrophotometer, perform dilution in accordance 1 ng/μl, 0.1 ng/μl, 0.01 ng/μl, 0.001 ng/μl, . . . , mix them with multiple non-rare blood group genome DNAs having the same volume, and then use the human rare blood group rapid screening method according to the present invention for multiplex PCR detection.

2. Experimental Steps (1) Extract six different positive control plasmids respectively, perform quantification with ultraviolet spectrophotometer, and then perform dilution according to proportions, to obtain positive control plasmids having different concentrations.

(2) Randomly select 4 non-rare blood group blood sample genome DNAs (No. 1-4) to mix them with equal volumes to obtain mixed DNAs, and the concentration of the mixed DNAs is 50-100 ng/μl; take six of the mixed DNAs, the volume of each mixed DNA is 3.20, and add 0.8 μl six different positive control plasmids after dilution to the six mixed DNAs, to form six Pools with a total volume of 4 μl and the number of samples being 5.

(3) Amplify the pools containing the corresponding control plasmids according to the Yt-K-Kpc system, the Dia-OK-Cob system or the Fyb-S system and the corresponding reaction condition, and the amplification products are detected by the gel imager after gel electrophoresis.

3. Experimental Results (1) Yt Plasmids

Figure 4:
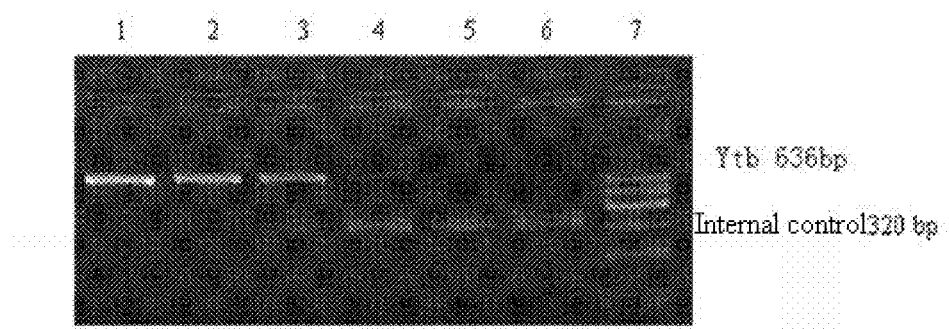
FIG. 4 illustrates gel imaging results of a Yt plasmid dilution experiment.

As shown in FIG. 4, Lanes 1-6: 3.2 μl mixed non-rare blood group blood sample genome DNA+0.8 μl Yt plasmids, and concentrations of the plasmids are 1 ng/μl, 0.1 ng/μl, 0.01 ng/μl, 0.001 ng/μl, 0.0001 ng/μl, 0.00001 ng/μl respectively; Lane 7: Marker, the fragments are 100, 200, 300, 400, 500, and 600 bp.

(2) K Plasmids

Figure 5:
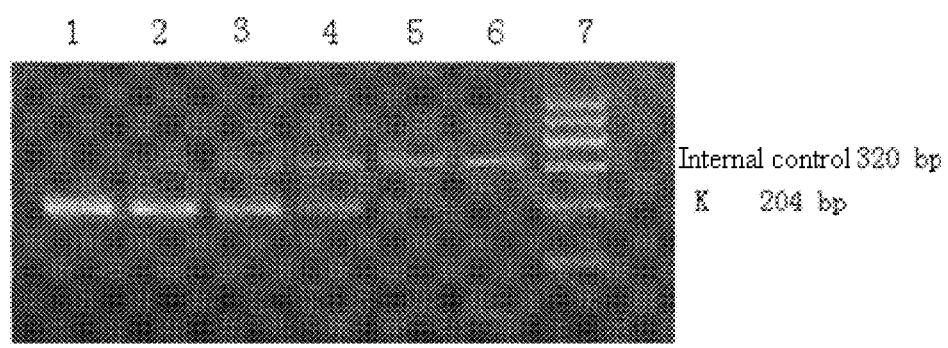
FIG. 5 illustrates gel imaging results of a K plasmid dilution experiment.

As shown in FIG. 5, Lanes 1-5: 3.2 μl mixed non-rare blood group blood sample genome DNA+0.8 μl K plasmids, and concentrations of the plasmids are 1 ng/μl, 0.1 ng/μl, 0.01 ng/μl, 0.001 ng/μl, 0.0001 ng/μl, 0.00001 ng/μl respectively; Lane 6: Marker, the fragments are 100, 200, 300, 400, 500, and 600 bp.

(3) Kpc Plasmids

Figure 6:
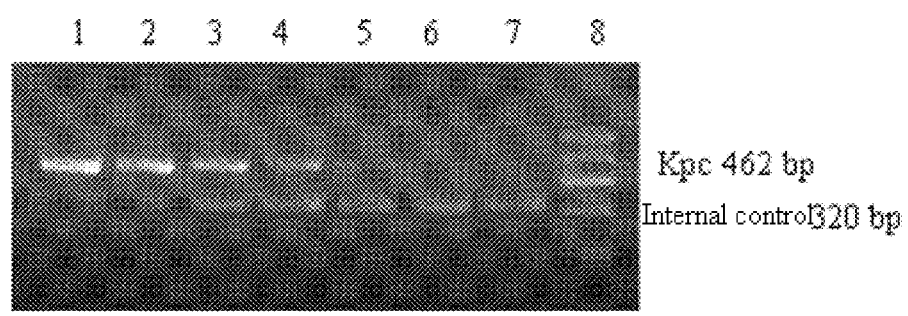
FIG. 6 illustrates gel imaging results of a Kpc plasmid dilution experiment.

As shown in FIG. 6, Lanes 1-7: 3.2 μl mixed non-rare blood group blood sample genome DNA+0.8 μl Kpc plasmids, and concentrations of the plasmids are 1 ng/μl, 0.1 ng/μl, 0.01 ng/μl, 0.001 ng/μl, 0.0001 ng/μl, 0.00001 ng/μl, 0.000001 ng/μl respectively; Lane 8: Marker, the fragments are 100, 200, 300, 400, 500, and 600 bp.

(4) Dia Plasmids

Figure 7:
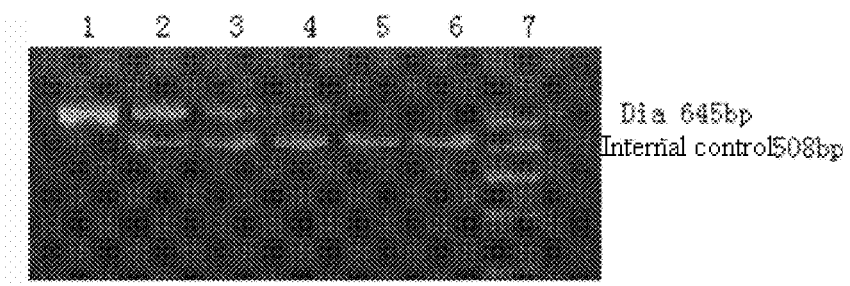
FIG. 7 illustrates gel imaging results of a Dia plasmid dilution experiment.

As shown in FIG. 7, Lanes 1-6: 3.2 μl mixed non-rare blood group blood sample genome DNA+0.8 μl Dia plasmids, and concentrations of the plasmids are 1 ng/μl, 0.1 ng/μl, 0.01 ng/μl, 0.001 ng/μl, 0.0001 ng/μl, 0.00001 ng/μl respectively; Lane 7: Marker, the fragments are 100, 200, 300, 400, 500, and 600 bp.

(5) Ok Plasmids

Figure 8:
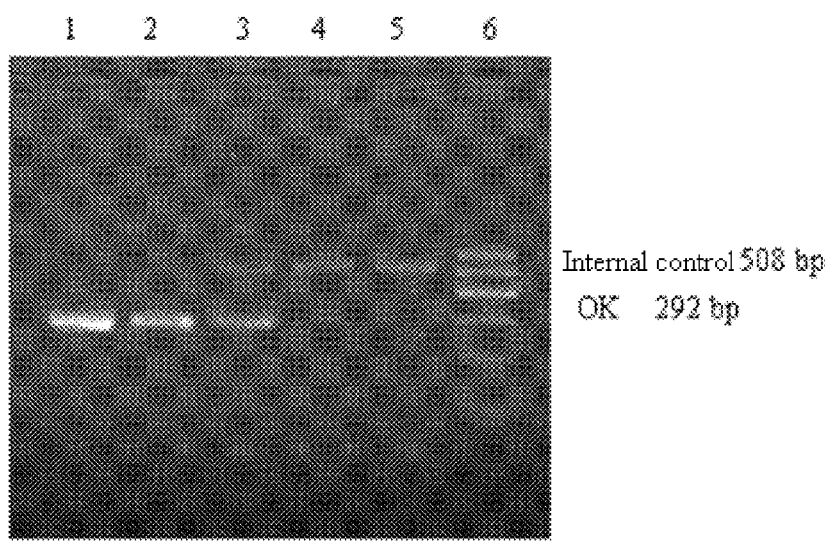
FIG. 8 illustrates gel imaging results of an OK plasmid dilution experiment.

As shown in FIG. 8, Lanes 1-5: 3.2 μl mixed non-rare blood group blood sample genome DNA+0.8 μl Dia plasmids, and concentrations of the plasmids are 1 ng/μl, 0.1 ng/μl, 0.01 ng/μl, 0.001 ng/μl, 0.0001 ng/μl respectively; Lane 6: Marker, the fragments are 100, 200, 300, 400, 500, and 600 bp.

(6) Cob Plasmids

Figure 9:
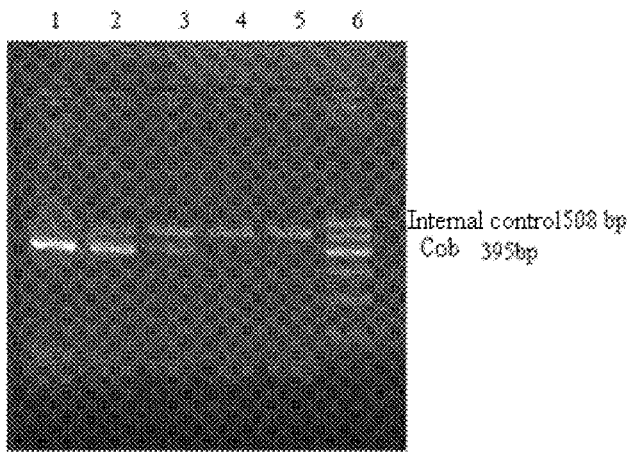
FIG. 9 illustrates gel imaging results of a Cob plasmid dilution experiment.

As shown in FIG. 9, Lanes 1-5: 3.2 μl mixed non-rare blood group blood sample genome DNA+0.8 μl Cob plasmids, and concentrations of the plasmids are 1 ng/μl, 0.1 ng/μl, 0.01 ng/μl, 0.001 ng/μl, 0.0001 ng/μl respectively; Lane 6: Marker, the fragments are 100, 200, 300, 400, 500, and 600 bp.

(7) Fyb Plasmids

Figure 10:
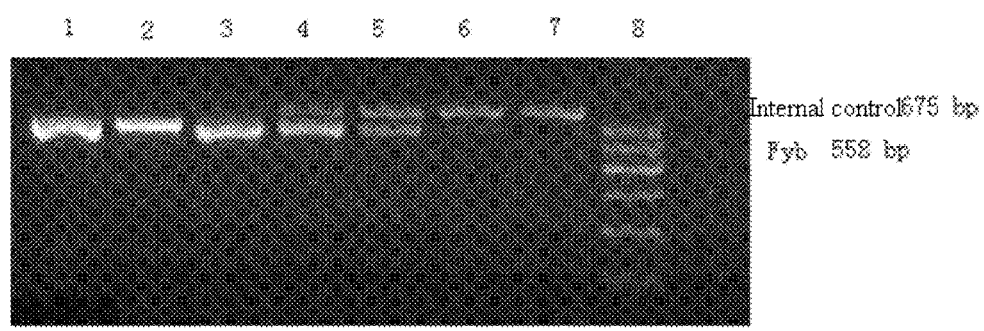
FIG. 10 illustrates gel imaging results of an Fyb plasmid dilution experiment.

As shown in FIG. 10, Lanes 1-7: 3.20 mixed non-rare blood group blood sample genome DNA+0.8 μl Fyb plasmids, and concentrations of the plasmids are 1 ng/μl, 0.1 ng/μl, 0.01 ng/μl, 0.001 ng/μl, 0.0001 ng/μl, 0.00001 ng/μl, 0.000001 ng/μl respectively; Lane 8: Marker, the fragments are 100, 200, 300, 400, 500, and 600 bp.

(8) S Plasmids

Figure 11:
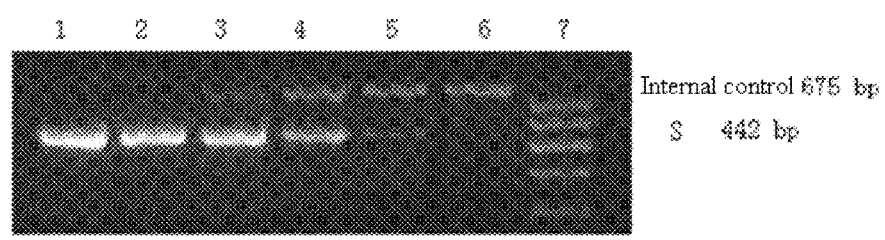
FIG. 11 illustrates gel imaging results of an S plasmid dilution experiment.

As shown in FIG. 11, Lanes 1-6: 3.2 μl mixed non-rare blood group blood sample genome DNA+0.80S plasmids, and concentrations of the plasmids are 1 ng/μl, 0.1 ng/μl, 0.01 ng/μl, 0.001 ng/μl, 0.0001 ng/μl, 0.00001 ng/μl respectively; Lane 7: Marker, the fragments are 100, 200, 300, 400, 500, and 600 bp.

It can be seen from the above experimental results that the rare blood group pool detection method of the present invention has higher sensitivity, which still can be detected even if the plasmid concentration is lower to 0.0001 ng/μl even 0.00001 ng/μl.

What is claimed is:

1. A multiplex PCR rapid screening method for screening human rare blood group, wherein the method comprises:
   (i) providing a test sample pool comprising mixed DNA templates extracted from blood samples obtained from multiple subjects;
   (ii) performing multiplex PCR amplification on the test sample pool using primers of SEQ ID NOS 7-12, wherein the primers amplify blood cell surface antigen genes containing low frequency SNPs of $Di^a$, OK274A, and $Co^b$;
   (iii) performing electrophoresis assay on the test sample pool that has been subjected to said multiplex PCR amplification;
   (iv) analyzing a detectable signal of the amplification products; wherein the presence of a signal corresponds to a positive detection of one or more homozygote having low-frequency SNP loci and/or one or more heterozygote having low-frequency SNP loci in the test sample pool;
   (v) providing one or more new test sample groups, wherein for said one or more new test sample groups, a different subset of the mixed DNA templates giving a positive detection signal are combined;
   (vi) repeating step (ii) to step (v) until the original positive sample has been determined; and
   (vii) performing a PCR-SSP or sequencing or serology methods to confirm whether the detected sample belongs to a rare blood group or is a heterozygote having rare blood group SNP loci.

2. The multiplex PCR rapid screening method of claim 1, wherein the test sample pool consist blood samples obtained from 5-12 subjects.

3. The multiplex PCR rapid screening method of claim 1, wherein the multiplex PCR amplification includes amplification of a positive amplification control; and wherein the emergence of a rare blood group electrophoretic band identical to the electrophoretic band corresponding to the positive control amplification indicates a positive detection of a rare blood group or a positive detection of a heterozygote having rare blood group SNP loci; wherein the absence of a rare blood group electrophoretic band at a location identical to the electrophoretic band of the positive control amplification indicates a negative detection of the rare blood group SNP loci.

4. The multiplex PCR rapid screening method of claim 3, wherein the positive amplification control is a plasmid containing a gene fragment comprising rare blood group SNP loci, and the positive amplification control comprise primer binding sites specific for SEQ ID NO: 7 and for SEQ ID NO: 8, or primer binding sites specific for SEQ ID NO: 9 and for SEQ ID NO: 10 or primer binding sites specific for SEQ ID NO: 11 and for SEQ ID NO: 12.

5. The multiplex PCR rapid screening method of claim 1, wherein a pair of internal control primers is in provided in step (ii); and wherein the emergence of both a rare blood group electrophoretic band and an internal control electrophoretic band indicates a positive detection result for a rare blood group or heterozygote having rare blood group SNP loci wherein the emergence of only an internal control electrophoretic band indicates a negative detection result of the rare blood group or heterozygote having rare blood group SNP loci; wherein the absence of both the rare blood group electrophoretic band and internal control electrophoretic band indicates that the detection has failed.

6. The multiplex PCR rapid screening method of claim 5, wherein the pair of internal control primers are SEQ ID NO: 19 and SEQ ID NO:20.

7. The multiplex PCR rapid screening method of claim 1, wherein said performing a multiplex PCR amplification consists forming a multiplex PCR reaction mixture comprising the test sample pool and the primers of SEQ ID NOS: 7-12 and wherein the multiplex PCR reaction mixture is held at 94° C. for 5 min, then subjected to thermocycling consisting a total of 35 cycles, each cycle consists a 94° C. incubation for 30s, a 60° C. incubation held for 30s, a 72° C. incubation held for 45s, and wherein following the thermocycling, a final extension step is performed, the final extension consists holding the multiplex PCR reaction mixture at 72° C. for 7 min.

8. The multiplex PCR rapid screening method of claim 1, wherein in step (v) if the number of the DNA templates having positive detection result in the pool is less than or equal to 5, each one of the DNA templates having positive detection result signal becomes a group.

* * * * *